US008382815B2

(12) United States Patent  
Malik et al.

(10) Patent No.: US 8,382,815 B2  
(45) Date of Patent: Feb. 26, 2013

(54) TIN$_x$C$_y$ MODIFIED SURFACE FOR AN IMPLANTABLE DEVICE AND A METHOD OF PRODUCING THE SAME

(75) Inventors: Shamim M. Malik, Temecula, CA (US); Avijit Mukherjee, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 54 days.

(21) Appl. No.: 12/535,948

(22) Filed: Aug. 5, 2009

(65) Prior Publication Data

US 2009/0299463 A1 Dec. 3, 2009

Related U.S. Application Data

(62) Division of application No. 09/997,450, filed on Nov. 30, 2001.

(51) Int. Cl.  
*A61F 2/06* (2006.01)  
*A61F 2/82* (2006.01)

(52) U.S. Cl. ..................................... 623/1.15

(58) Field of Classification Search .............. 623/1.15; 427/2.24, 2.25, 2.3, 2.26, 528, 530; 422/50, 422/63, 500; 424/400, 409, 417, 422, 423, 424/484; 435/289.1, 293.1, 299.1  
See application file for complete search history.

(56) References Cited

U.S. PATENT DOCUMENTS

| | | | |
|---|---|---|---|
| 4,486,247 A | 12/1984 | Ecer et al. | |
| 4,603,704 A * | 8/1986 | Mund et al. | 607/116 |
| 4,886,062 A * | 12/1989 | Wiktor | 606/194 |
| 5,040,548 A | 8/1991 | Yock | |
| 5,047,050 A | 9/1991 | Arpesani | |
| 5,049,132 A | 9/1991 | Shaffer et al. | |
| 5,074,313 A * | 12/1991 | Dahl et al. | 607/119 |
| 5,084,151 A | 1/1992 | Vallana et al. | |
| 5,165,919 A | 11/1992 | Sasaki et al. | |
| 5,188,734 A | 2/1993 | Zepf | |
| 5,192,311 A | 3/1993 | King et al. | |
| 5,336,518 A * | 8/1994 | Narayanan et al. | 427/470 |
| 5,415,704 A * | 5/1995 | Davidson | 148/316 |
| 5,800,747 A | 9/1998 | Cavasin | |
| 5,925,552 A | 7/1999 | Keogh et al. | |
| 5,954,761 A | 9/1999 | Machek et al. | |
| 6,099,457 A | 8/2000 | Good | |
| 6,110,204 A * | 8/2000 | Lazarov et al. | 623/11.11 |
| 6,231,956 B1 | 5/2001 | Brenner et al. | |
| 6,273,908 B1 | 8/2001 | Ndondo-Lay | |
| 6,273,913 B1 | 8/2001 | Wright et al. | |
| 6,335,029 B1 | 1/2002 | Kamath et al. | |
| 6,519,488 B2 | 2/2003 | KenKnight et al. | |
| 6,520,923 B1 | 2/2003 | Jalisi | |
| 6,613,432 B2 | 9/2003 | Zamora et al. | |
| 6,632,470 B2 | 10/2003 | Morra et al. | |
| 6,676,989 B2 * | 1/2004 | Kirkpatrick et al. | 427/2.28 |
| 7,056,523 B1 | 6/2006 | Michal et al. | |

(Continued)

FOREIGN PATENT DOCUMENTS

DE 19855786 6/2000

OTHER PUBLICATIONS

U.S. Appl. No. 09/997,449, filed Nov. 30, 2001, Malik et al.

(Continued)

*Primary Examiner* — Ryan Severson  
(74) *Attorney, Agent, or Firm* — Squire Sanders (US) LLP

(57) ABSTRACT

Implantable devices, such as stents, having a surface modified with TiN$_x$C$_y$ are disclosed.

4 Claims, 3 Drawing Sheets

U.S. PATENT DOCUMENTS

| | | |
|---|---|---|
| 7,077,860 B2 | 7/2006 | Yan et al. |
| 7,163,165 B2 | 1/2007 | Paul et al. |
| 7,163,715 B1 | 1/2007 | Kramer |
| 7,201,940 B1 | 4/2007 | Kramer |
| 7,441,513 B1 | 10/2008 | Malik et al. |
| 2003/0004596 A1 | 3/2003 | Lazarov et al. |
| 2003/0175444 A1 | 9/2003 | Huang et al. |
| 2006/0178738 A1 | 8/2006 | Yan et al. |
| 2007/0036905 A1 | 2/2007 | Kramer |
| 2007/0166496 A1 | 7/2007 | Kramer |
| 2007/0184228 A1 | 8/2007 | Kramer |

OTHER PUBLICATIONS

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Scheuer et al., *Model of plasma source ion implantation in planar, cylindrical, and spherical geometries*, J. Appl. Phys., vol. 67, No. 3, pp. 1241-1245 (Feb. 1990).

Shamim et al., *Measurement of electron emission due to energetic ion bombardment in plasma source ion implantation*, J. Appl. Phys., vol. 70, No. 9, pp. 4756-4759 (Nov. 1991).

Shamim et al., *Measurements of Spatial and Temporal Sheath Evolution for Spherical and Cylindrical Geometries in Plasma Source Ion Implantation*, J. Appl. Phys., vol. 69, No. 5, pp. 2904-2908 (Mar. 1991).

Windecker et al., *Stent Coating with Titanium-Nitride-Oxide for Reduction of Neointimal Hyperplasia*, Circulation, Aug. 21, 2001; 104:928-933.

http://www.bbw.admin.ch/abstracts/abstr2000/abstracts/biomed/bm95.0439.html, Windecker et al., *Stent Coating for Prevention of Instent-Restenosis*, Reporting Date Dec. 31, 1999, printed May 23, 2002.

\* cited by examiner

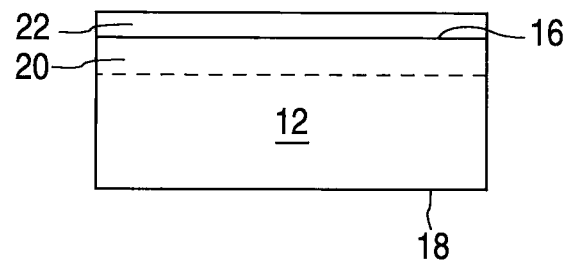
Figure 2C1
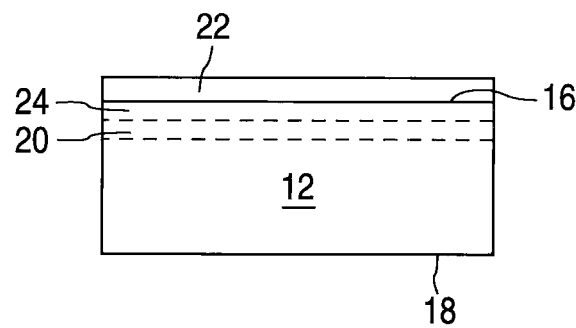
Figure 2C2
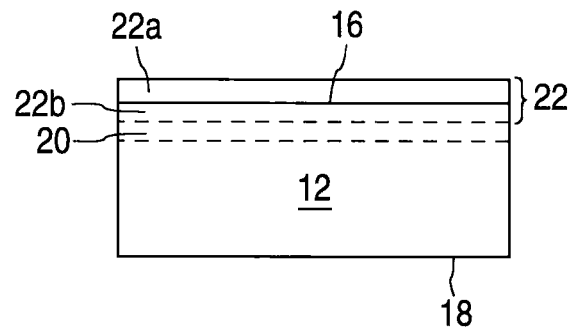
Figure 2C3

$TiN_xC_y$ MODIFIED SURFACE FOR AN IMPLANTABLE DEVICE AND A METHOD OF PRODUCING THE SAME

CROSS-REFERENCE TO RELATED APPLICATION

This is a divisional of application Ser. No. 09/997,450 filed on Nov. 30, 2001, which is incorporated by reference as if fully set forth, including any figures, herein.

BACKGROUND OF THE INVENTION

1. Field of the Invention

The present invention relates generally to implantable devices, such as stents. More particularly, the invention relates to an implantable device having a modified surface and a method of modifying the surface.

2. Description of the Background

Blood vessel occlusions are commonly treated by mechanically enhancing blood flow in the affected vessel, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents can be coated with various materials so as to provide therapeutic benefits in the treatment of an occluded vessel. For example, a stent can be coated with materials that provide the stent with increased biocompatibility, with lubrication for ease of positioning, with radiopacity or radioactivity for visualization, and with drug delivery capabilities.

It has been reported that coronary artery stents coated with titanium nitride oxide reduce neointimal hyperplasia in the porcine restenosis model. (Stephan Windecker et al., "Stent Coating with Titanium-Nitride-Oxide for Reduction of Neointimal Hyperplasia," Swiss Cardiovascular Center, University Hospital, Bern, Switzerland.) Neointimal hyperplasia generally refers to vascular smooth muscle cell migration and proliferation in response to an injury caused by intravascular interventions such as stenting. It is believed that neointimal hyperplasia contributes, at least in part, to restenosis, which is the re-narrowing of the vessel within weeks or months following intravascular treatment. Blood vessels in which significant restenosis occurs typically require further treatment. Accordingly, it is desirable to minimize neointimal hyperplasia and restenosis.

SUMMARY

In accordance with one aspect of the embodiments of the present invention, a medical device, such as a stent, is provided having a $TiN_xO_y$ compound implanted at a depth within at least a region of a surface of the stent. The depth of the implanted $TiN_xO_y$ compound can be less that 2000 angstroms from the surface of the stent. In one embodiment, a layer of $TiN_xO_y$ compound can be deposited on the region of the surface of the stent where the $TiN_xO_y$ compound is implanted. The stent can be made out of any suitable metallic material or alloy. The stent can, for example, be made from stainless steel. The surface of the stent being modified can be the outer or the tissue-contacting surface of the stent. In accordance with yet another embodiment, a layer of Ti, N, or TiN can be deposited beneath the layer of $TiN_xO_y$.

In accordance with another aspect of the invention, a device, such as a stent, is provided having a surface and a $TiN_xC_y$ compound deposited on at least a region of the surface of the device. In accordance with another aspect of the invention, a device, such as a stent, is provided having a surface and a $TiN_xC_y$ compound implanted at a depth within at least a region of the surface of the stent.

In accordance with yet another aspect of the invention, a method of modifying a surface of a device, such as a stent, is provided, which method comprises implanting a $TiN_xO_y$ compound at a depth within a surface of the stent. The method can additionally comprise depositing a layer of a $TiN_xO_y$ compound on the surface of the stent where the $TiN_xO_y$ compound is implanted.

In accordance with another aspect of the invention, a method of modifying a surface of a device, such as a stent is provided, which method comprises implanting Ti, N, or TiN into the surface of the stent and forming a layer of the $TiN_xO_y$ compound over the areas where Ti, N, or TiN has been implanted.

In accordance with yet another aspect of the invention, a method of modifying a surface of a device, such as a stent, is provided, which method comprises implanting a $TiN_xC_y$ compound at a depth within a surface of the stent or depositing the compound on the surface of the stent.

BRIEF DESCRIPTION OF THE FIGURES

FIGS. 2A, 2B, and 2C1, 2C2, and 2C3 illustrate process steps for modifying a stent surface and modified stent surfaces in accordance with embodiments of the invention; and FIG. 3 schematically illustrates one embodiment of a reaction chamber that can be used to carry out the processes of the present invention.

DETAILED DESCRIPTION

A surface of a medical device can be modified so as to include titanium nitride oxide or a titanium nitride carbide. A medical device is broadly defined to include any implantable device such as any inter- or intraluminal device used for the release of an active agent, for upholding luminal patency, or for any other treatment purposes in a human or veterinary patient. Examples of such medical devices include self-expandable stents, balloon-expandable stents, stent-grafts, grafts (e.g., aortic grafts), artificial heart valves, cerebrospinal fluid shunts, axius coronary shunts, pacemaker electrodes, and endocardial leads (e.g., FINELINE and ENDOTAK, available from Guidant Corporation). The underlying structure of the device can be of virtually any design. The device can be made of a metallic material or an alloy. Stainless steel is one example of a commonly used material.

Figure 1:
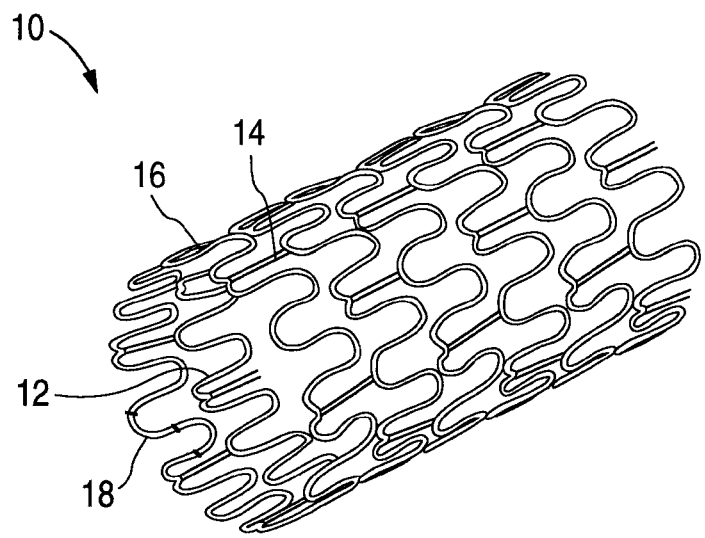
FIG. 1 is a perspective view of a conventional stent having a scaffolding structure.
Figure 2A:
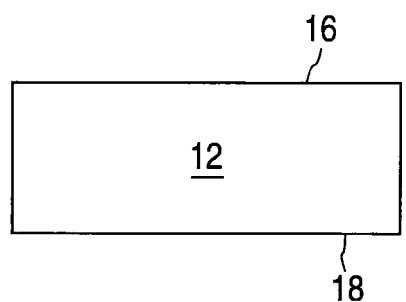

The present invention will be described with reference to a stainless steel stent. FIG. 1 illustrates one example of a conventional stent 10, the structure of which can include struts 12 connected by elements 14. Struts 12 and elements 14 define a tubular body having an outer or tissue contacting surface 16 and an inner surface 18. FIG. 2A illustrates a section of one of the struts 12 as will be modified as described hereinafter. It is understood that any portion of outer surface 16, including selected areas of elements 14 can be similarly treated and that the modification is not limited to any particular region of outer surface 16 or inner surface 18 of stent 10.

Figure 3:
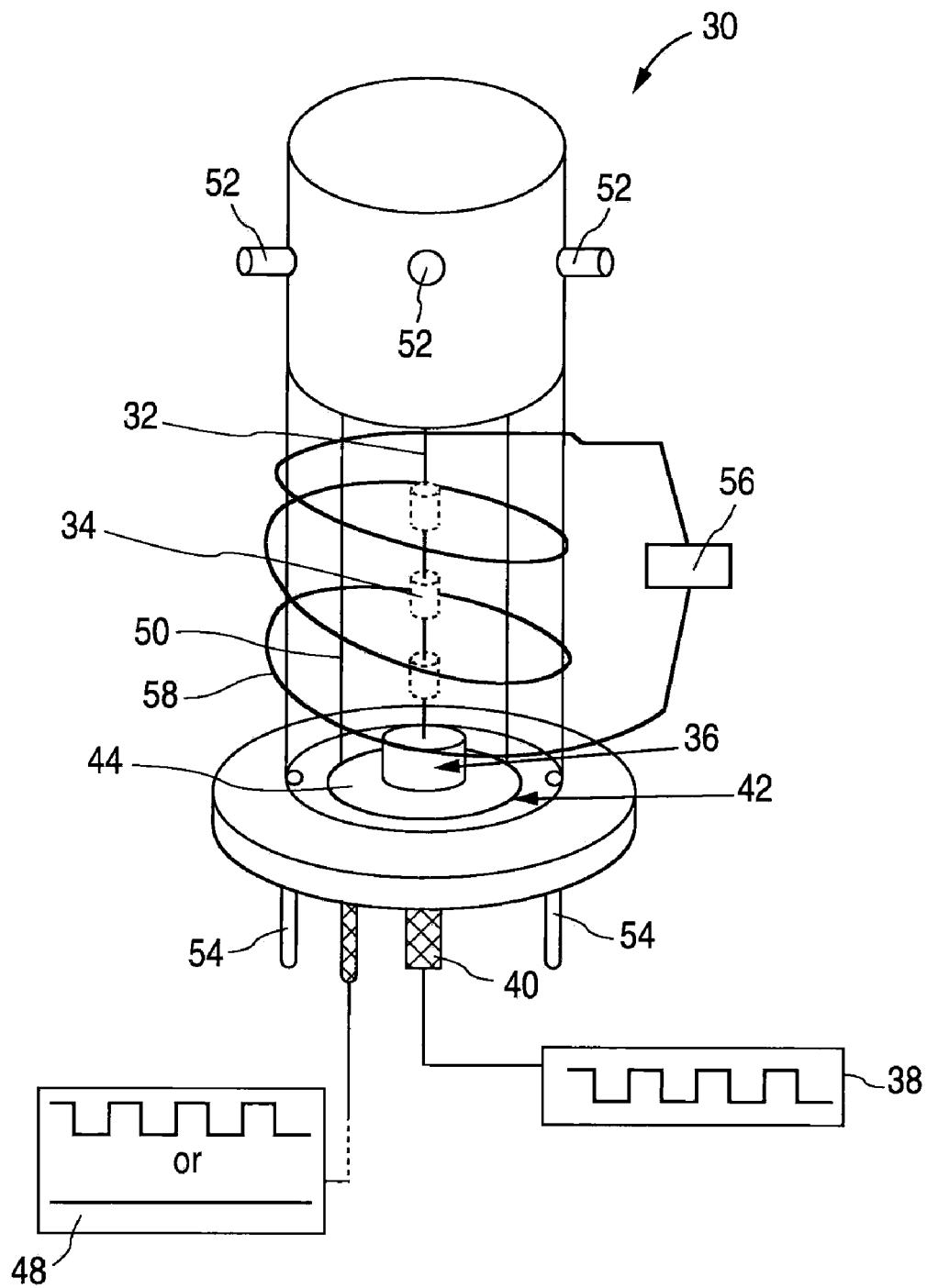

Prior to surface modification of stent 10, outer surface 16 (including inner surface 18) is cleaned by argon ion bombardment. Stent 10 can be placed on a mandrel and positioned within a reaction chamber. One example of a suitable system for carrying out the process is illustrated in FIG. 3, the details of which are described later in the specification. Argon gas (e.g., >99.9% by volume) can be introduced in the reaction chamber (having a volume of, for example, 2000 cm³) at a flow rate of about 10 to 200 sccm, for example at about 50 sccm. The pressure of the chamber can be about 50 mTorr. The RF power and frequency can be, for example, about 100 Watts and 13.56 MHz, respectively. The bias voltage applied to the stent can be from about 100 V to about 3 KV, for example about 1 KV. The cleaning process can be conducted for about 5 minutes to about 30 minutes in duration.

In one embodiment, following the act of cleaning stent 10, nitrogen ions can be implanted in surface 16 of the stent. Nitrogen can be implanted by introduction of a nitrogen gas in the chamber followed by initiation of plasma under the parameters illustrated in Table 1:

TABLE 1

| Process | Parameter Range | Exemplary Value |
| --- | --- | --- |
| nitrogen | — | >99.9% by volume |
| gas flow rate (sccm) | 10 to 200 | 40 |
| volume of chamber (cm³) | — | 2000 |
| pressure (mTorr) | 0.1 to 2 | 0.5 |
| RF power (watts) | 10 to 1000 | 200 |
| RF frequency MHz | 0.2 to 2450 | 13.56 |
| bias voltage stent (KV) | −20 to −60 | −50 |
| bias voltage titanium grid (KV) | −20 to −60 | −45 |
| thickness (or depth) of the implant (Å) | 500 to 2000 | 800 |

Figure 2B:
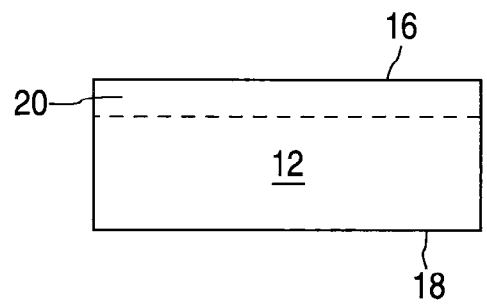

FIG. 2B illustrates nitrogen implanted within surface 16, as indicated by region 20. It should be noted that the presence of a titanium grid in the reaction chamber during the implantation procedure of nitrogen does not lead to any significant sputtering of the titanium from the grid and onto stent 10 as the nitrogen ions should be essentially incapable of sputtering the titanium off the grid.

In accordance with another embodiment, in lieu of implanting nitrogen at a selected depth within outer surface 16 of stent 10, titanium can be implanted into outer surface 16. This can be accomplished by using an argon gas (e.g., >99.9% by volume) instead of the nitrogen gas. The process parameters that are similar to that of Table 1 can be employed to form a titanium implant at similar depths. The purpose of nitrogen or titanium implantation is to provide a more suitable platform for modification of the surface into $TiN_xO_y$ or $TiN_xC_y$.

Surface modification can be accomplished by introducing argon in the reaction chamber and initiating plasma to sputter titanium off the grid and on or into surface 16. A source gas containing oxygen and nitrogen can also be introduced into the reaction chamber for reacting with the titanium to form $TiN_xO_y$. By way of example, in an embodiment in which the source gas is nitrogen monoxide (NO), $NO^-$ ions will react with titanium ions to form a titanium nitride monoxide (TiNO). Similarly, in an embodiment in which the source gas is nitrogen dioxide ($NO_2$), $NO_2^-$ ions and dissociated $NO^-$ ions will mix with titanium ions to form a mixture of titanium nitride dioxide ($TiNO_2$) and titanium nitride monoxide (TiNO). Windecker et al. has reported that coronary artery stents coated with titanium nitride dioxide or titanium nitride monoxide reduced neointimal hyperplasia in pigs by 47% and 44%, respectively.

Process parameters for modifying the surface as to include $TiN_xO_y$ are illustrated in Table 2:

TABLE 2

| Process | Parameter Range | Exemplary Value |
| --- | --- | --- |
| gases (by volume) | argon: 20% to 80%<br>oxygen: 10% to 40%<br>nitrogen: 10% to 40% | argon: 20%<br>oxygen: 40%<br>nitrogen: 40% |
| gas flow rate (sccm) | 10 to 200 | 30 |
| volume of chamber (cm³) | — | 2000 |
| pressure (mTorr) | 0.1 to 500 | 50 |
| RF power (watts) | 10 to 1000 | 100 |
| RF frequency MHz | 0.2 to 2450 | 13.56 |
| bias voltage stent (KV) | −5 to −30 | −10 |
| bias voltage grid (KV) | −5 to −30 | −9 |
| thickness of layer 22 (Å) | 1000 to 50,000 | 5000 |

The negative voltage applied to stent 10 can have a frequency of up to, for example, 500 KHz, and a width of 70 to about 200 microseconds. In one embodiment, as illustrated in FIG. 2C1, a $TiN_xO_y$ layer 22 is formed on the nitrogen or titanium region 20. In accordance with another embodiment, the nitrogen gas can be introduced into the chamber prior to the introduction of the combination of the oxygen and nitrogen gases. Accordingly, region 20 may include traces of TiN or alternatively, as illustrated in FIG. 2C2, a layer of TiN, as illustrated by reference number 24, may be implanted in surface 16 followed by formation of $TiN_xO_y$ layer 22 when oxygen is introduced in the chamber. In yet an alternative embodiment, as illustrated in FIG. 2C3, some of the $TiN_xO_y$ can be implanted within surface 16, as illustrated by region 22b, in addition to having $TiN_xO_y$ deposited on surface 16, as illustrated by region 22a. Region 22b can be from about 500 Å to about 2000 Å in depth. As is understood by one of ordinary skill in the art, a variety of modifications can be made to the process parameters so as to achieve a particular cross-sectional topography.

In accordance with another embodiment in which the source gases are nitrogen and methane ($CH_4$), nitrogen and carbon ions will mix with titanium to form a titanium nitride carbide ($TiN_xC_y$) species. Titanium nitride carbides are hard materials that are corrosion-resistant and have excellent biocompatibility properties. The ratio of nitrogen to carbon, and thus the particular properties of the modified surface, can be controlled by controlling the concentrations and/or flow rates of the respective gases into the reaction chamber.

Example of the Reaction Chamber

The above-described methods can be performed by any suitable apparatus known to one of ordinary skill in the art. One example of such plasma reaction chamber 30 is illustrated in FIG. 3. Chamber 30 can be cylindrical in shape and can be fabricated from any number of suitable materials, such as, stainless steel, glass, and aluminum. By way of example, chamber 30 can be from about 4 inches (10.16 cm) to about 15 inches (38.1 cm) in diameter and from about 5 inches (12.7 cm) to about 18 inches (45.72 cm) in height.

A mandrel 32 holds a single medical device 34 (e.g., stent 10) or multiple medical devices 34 in position relative to the interior walls of chamber 30. Medical device 34 can be oriented at any position within chamber 30 as required to achieve a desired implantation or deposition. One end of mandrel 32 can be coupled to an electrode 36.

Electrode 36 can be made from of any suitable electrically conductive material including, but not limited to, steel, copper, chromium, nickel, tungsten, iron, and similar materials. A first power source 38, electrically coupled to electrode 36 via electrical feedthrough port 40, can apply negative voltage pulses to electrode 36.

In one embodiment, an insulator 42, formed of a non-electrically conductive material, including materials such as rubber, ceramic, or plastic, is provided. Insulator 42 can include a connector 44, which can be either electrically coupled to first power source 38 or an independent second power source 48 for applying a voltage to a sputtering grid 50.

Sputtering grid 50 can be positioned within chamber 30 in symmetrical conformity about medical device 34 so as to allow equal bombardment of device 24 from all directions. Sputtering grid 50 can be manufactured from titanium or, alternatively, can be made of a base material that is coated with titanium. Sputtering grid 50 can be cylindrically shaped. Sputtering grid 50 can be of solid construction or perforated. By way of example, sputtering grid 50 can be a perforated cylinder measuring approximately 0.5 inches (1.27 cm) to 3.0 inches (7.62 cm) in diameter, approximately 2 inches (5.08 cm) to 12 inches (30.48 cm) in height, and approximately 1/32 of an inch (0.08 cm) thick. The diameter of the perforations can be from about 0.125 inches (0.318 cm) to about 0.25 inches (0.635 cm). The percentage of the grid occupied by perforation, as opposed to titanium sputtering material, can be from about 40% to about 80% of the total surface area.

Gas ports 52 can be positioned on top of chamber 30, while aspiration ports 54 can positioned at or near the base of chamber 30. Gas ports 52 are used to flux a gaseous medium in liquid or vapor form into chamber 30, where it is converted into ionized plasma. Aspiration ports 54 are used after processing is complete, or when a new gas is desired, to purge chamber 30.

Additionally, an apparatus for accomplishing the method of the present invention includes a plasma-generating means. The plasma-generating means can be, for example, a radio frequency source and antenna, a microwave source, or any other suitable element known to one of ordinary skill in the art. By way of example, FIG. 3 illustrates a radio frequency source 56, such as that manufactured by Dressler of Germany, and an antenna 58. In one such embodiment, antenna 58 can be a radio-frequency conducting filament that is wrapped about chamber 30 in a helical or corkscrew-like fashion.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. An implantable medical device comprising a $TiN_xC_y$ compound deposited on at least a region of a surface of the device;
    wherein
    the device further comprises only N or only Ti implanted at a depth within at least the region of the surface of the device, and wherein the $TiN_xC_y$ compound is deposited above the region implanted with N or Ti;
    or
    the device further comprises only TiN implanted at a depth within at least the region of the surface of the device with the $TiN_xC_y$ compound being deposited above the region implanted with TiN;
    or
    the device further comprises
        a first region comprising only N or only Ti implanted at a depth within at least the region of the surface of the device; and
        a second region over the first region, and the second region comprising only TiN implanted at a depth within at least the region of the surface of the device; and
        the $TiN_xC_y$ compound is deposited over the second region.

2. The implantable medical device of claim 1, wherein the device further comprises only N or only Ti implanted at a depth within at least the region of the surface of the device, and wherein the $TiN_xC_y$ compound is deposited above the region implanted with N or Ti.

3. The implantable medical device of claim 1, wherein the device further comprises only TiN implanted at a depth within at least the region of the surface of the device with the $TiN_xC_y$ compound being deposited above the region implanted with TiN.

4. The implantable medical device of claim 1, wherein the device further comprises
    a first region comprising only N or only Ti implanted at a depth within at least the region of the surface of the device; and
    a second region over the first region, and the second region comprising only TiN implanted at a depth within at least the region of the surface of the device; and
    the $TiN_xC_y$ compound is deposited over the second region.

* * * * *

UNITED STATES PATENT AND TRADEMARK OFFICE
CERTIFICATE OF CORRECTION

| | | |
|---|---|---|
| PATENT NO. | : 8,382,815 B2 | Page 1 of 1 |
| APPLICATION NO. | : 12/535948 | |
| DATED | : February 26, 2013 | |
| INVENTOR(S) | : Malik et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Eighth Day of October, 2013

Teresa Stanek Rea
*Deputy Director of the United States Patent and Trademark Office*